United States Patent [19]
Schumacher

[11] Patent Number: 5,697,787
[45] Date of Patent: Dec. 16, 1997

[54] DENTAL INSERTS

[76] Inventor: Dieter Schumacher, Beselerstr. 2, 24768 Rendsburg, Germany

[21] Appl. No.: 497,363

[22] Filed: Jun. 30, 1995

[30] Foreign Application Priority Data

Jul. 14, 1994 [DE] Germany .............. 9410836 U
Oct. 28, 1994 [DE] Germany .............. 44 38 573.0

[51] Int. Cl.$^6$ .............. A61C 5/04; A61C 3/08
[52] U.S. Cl. .............. 433/226; 433/164
[58] Field of Search .............. 433/226, 204, 433/217.1, 164, 222.1

[56] References Cited

U.S. PATENT DOCUMENTS

| | | | |
|---|---|---|---|
| 532,721 | 1/1895 | Dennis | 433/164 |
| 983,579 | 2/1911 | Taggart | 433/226 |
| 3,657,780 | 4/1972 | Stolte | 29/148.4 R |
| 3,693,972 | 9/1972 | Minchin | 273/58 |
| 4,234,310 | 11/1980 | Leuthard | 433/228 |
| 4,744,759 | 5/1988 | Bowen | 433/228 |
| 4,993,951 | 2/1991 | Schumacher | 433/226 |
| 5,203,203 | 4/1993 | Bryan et al. | 73/54.19 |
| 5,219,283 | 6/1993 | Farzin-Nia et al. | 433/9 |
| 5,377,552 | 1/1995 | Kley | 73/862.49 |

*Primary Examiner*—Edgar S. Burr
*Assistant Examiner*—Dave A. Ghatt
*Attorney, Agent, or Firm*—Westman, Champlin & Kelly, P.A.

[57] ABSTRACT

Dental inserts for stopping or filling a cavity of a carious tooth treated by preparation. The inserts have a spherical or hemispherical shape and are matched to the particular drilling and plugging instruments.

2 Claims, 1 Drawing Sheet

DENTAL INSERTS

BACKGROUND OF THE INVENTION

The invention relates to dental inserts for filling or stopping a cavity of a human tooth which has been treated by preparation.

Dental cavities are filled either solely with a plastic material or with a plastic material having an additional inlay. Use is made of inlays, because the known tooth-coloured, plastic stopping materials have inadequate material characteristics. The inlays reduce these material-caused disadvantages and thereby ensure a longer life for the stopping.

Hitherto inlays have been generally produced from a model obtained from an impression of the cavity to be treated. Through the improvement of the tooth-coloured stopping materials use is increasingly being made of ready-made, pre-fabricated inlays or so-called inserts.

Such known inserts are e.g. described in U.S. Pat. No. 4,234,310. The shapes of the known inserts extend from simple triangular cross-sections to very complex shapes. An attempt is made by special grooves on the outside to obtain a better hold.

The known inserts have hitherto only partly satisfied practical requirements. For very irregularly shaped cavities, e.g. for those having a sinuous configuration, but also for round occlusal—approximal cavities, the known inserts are scarcely suitable. In addition, such inserts are more difficult to manufacture and coat and are consequently expensive.

The problem of the invention is to so further develop the inserts that they are suitable for all cavity shapes and can be easily manufactured and applied, whilst decisively improving quality in the finished stopping.

SUMMARY OF THE INVENTION

The present invention relates to dental inserts for stopping a tooth cavity after the tooth has been prepared.

The inserts are advantageously given a spherical shape and are made from dental ceramic, composite material or glass and are advantageously made in light-conducting and at least transparent manner. Nowadays dental ceramics, such as e.g. beta-quartz, often consist of a quartz-glass-ceramic, whose surfaces facilitate the adhesion of the stopping or adhesive material, i.e. are adhesion-active and are well joined to the plastic stopping material. The adhesion of e.g. composite adhesive or compomer can be improved by silanizing the covering with e.g. organic silicon compounds. Dental ceramic permits the treatment with the conventionally used diamond tools, without requiring special tools.

As spherical inserts are undirected, they can easily be inserted in all cavity shapes, without having to be oriented in a complicated manner. Cavities can be more simply spherically prepared, because during preparation no angular orientations have to be respected. The same advantages are obtained with inserts in which most of the surface is spherical, but which have a flat top or a retaining portion.

Spherical inserts are compressed during insertion in advantageous directions to the plastic stopping material in irregular cavities and achieve the best results if the cavity is trimmed with spherical drills and spherical pluggers, it being simple to adapt to the corresponding sphere diameter the inserts shaped in the same was in all directions, because only one dimension, i.e. the diameter determines the choice of tool. In addition, a reliable stopping of the cavity is obtained, because no recess on the edge of the insert or optionally the surface of the insert allows a larger-surface contact with the spatula or application syringe and consequently during the removal of said spatula or said syringe the cavity is not partly emptied by the fact that partial quantities adhering to the spatula or syringe are also removed with the same.

Further advantages are the reduction of the polymerization shrinkage, which prevents marginal gaps. In addition, the spherical shape ensures that any form of edge will not lead to stress peaks in the material shrinking during curing and consequently prevents marginal gaps. The roundness of the insert brings about an optimum adjustment of all the stresses. In addition, the abrasion strength and modulus of elasticity are increased. The hitherto known stopping materials are not completely abrasion-resistant and only permit a limited service life due to their relative elasticity.

The inserts also increase the light penetration depth when using light-curing materials. Hitherto a stopping has had to be cured layerwise due to the limited light penetration depth. It is now possible to polymerize the complete stopping in a single operation, because the inserts focus the light and transfer it into the deep areas of the stopped cavity. As a result of their spherical lens characteristics inserts can provide an advantageous location for the focus.

DESCRIPTION OF THE DRAWINGS

The invention is described in greater detail hereinafter relative to non-limitative embodiments and the attached drawings, wherein show.

DESCRIPTION OF PREFERRED EMBODIMENTS

Figure 1:
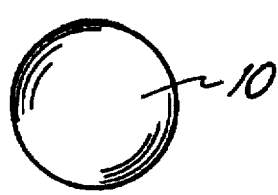
FIG. 1 The spherical insert.
Figure 2:
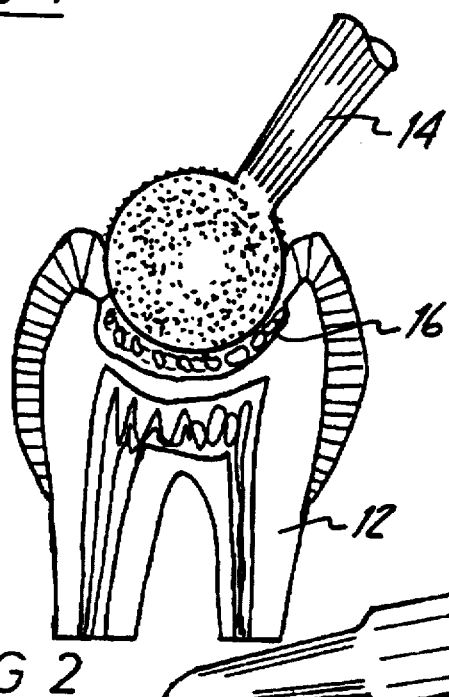
FIG. 2 A side view of the tooth with a spherical drill during preparation of the cavity.
Figure 4:
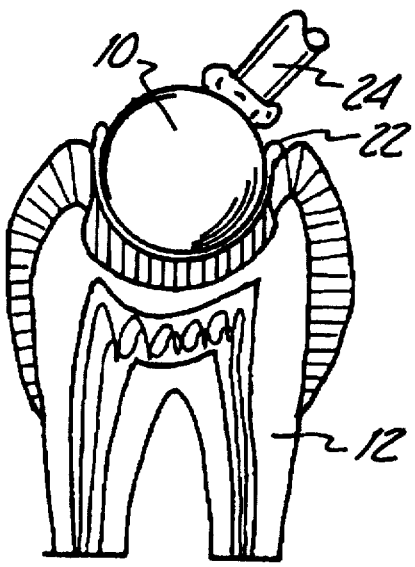
FIG. 4 A side view of the tooth with the spherical insert.
Figure 5:
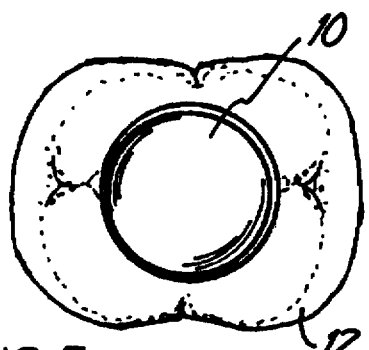
FIG. 5 A plan view of the tooth with the spherical insert.
Figure 3:
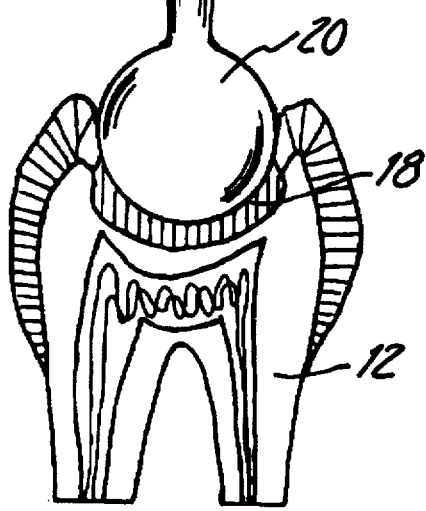
FIG. 3 A side view of the tooth with the spherical plugger in a shallow cavity.

The simplest use of the spherical insert consists of pressing it into the plastic stopping material, followed by curing. The following procedure should be adopted to obtain perfect results. The cavity of the tooth 12 is prepared, the caries 16 excavated, followed by trimming with the optimum spherical drill 14. An understopping 18 is applied to protect the pulpa, followed by compression and shaping with a spherical plugger 20. The insert matched to the spherical plugger is now selected. The prepared cavity is partly filled or stopped with the plastic filling or stopping material 22 from an application syringe 24 (FIG. 4), the insert 10 with the sticky stopping material projecting from the syringe is removed from a container and pressed into the cavity.

The insert is then pressed until it meets the cavity and is cured. The cavity surface is now finished.

In order to prepare larger, shallow cavities, it is advantageous to use hemispherical inserts, which consist of an insert portion 28 (FIG. 6) and the retaining portion 30, which in the same way as the top of the sphere is polished during the subsequent finishing of the cavity.

Figure 6:
FIG. 6 A hemispherical insert in side view.
Figure 7:
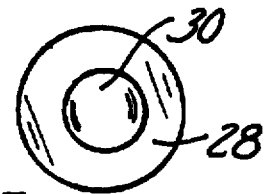
FIG. 7 A hemispherical insert in plan view.

The hemispherical inserts of FIGS. 6 and 7 are advantageously applied with forceps.

Through the use of silanized surfaces and the application of an adhesive, it is also possible when even very small surfaces are made available for the inserts and despite the lack of retaining edges, to securely hold the same in the cavity.

When dimensioning the insert only a single dimension, namely the diameter has to be measured. This is much simpler than in the case of the known inserts with their complex shapes.

What is claimed is:

1. A method of stopping a tooth cavity, comprising the steps of:

trimming with a spherical drill to form a part spherical surface in the tooth cavity;

applying an understopping material on the trimmed surface in the cavity;

compressing and shaping the understopping material with a spherical plugger to form a part spherical seat; and filling the part spherical seat with an insert having at least a part spherical outer surface and held in place with a filling material, said part spherical outer surface of the insert being slightly smaller than the part spherical seat.

2. The method of claim 1, wherein the insert is a complete sphere, and including the step of polishing an exposed portion of the insert after the insert is held in place in the tooth cavity.

* * * * *